United States Patent [19]

Fierro, Jr. et al.

[11] Patent Number: 5,837,272
[45] Date of Patent: Nov. 17, 1998

[54] PROCESS FOR FORMING STABLE GELLED AQUEOUS COMPOSITION

[75] Inventors: Louis Anthony Fierro, Jr., Clifton; Gregory M. Renga, Princeton; Joseph Frank Stima, Edison, all of N.J.

[73] Assignee: Colgate Palmolive Company, Piscataway, N.J.

[21] Appl. No.: 764,372

[22] Filed: Dec. 13, 1996

[51] Int. Cl.⁶ .............................. A61K 7/00; B01F 11/02; B01J 13/00
[52] U.S. Cl. ...................... 424/401; 252/314; 252/315.3; 252/315.4; 366/127; 510/383; 510/403; 514/944; 524/916; 526/932
[58] Field of Search .................................. 252/314, 315.3, 252/315.4; 510/383, 403; 524/916; 526/932; 366/127; 424/401; 514/944

[56] References Cited

U.S. PATENT DOCUMENTS

| | | | |
|---|---|---|---|
| 1,392,849 | 10/1921 | Plauson | 252/315.4 X |
| 2,019,363 | 10/1935 | Schulz | 252/315.3 |
| 3,176,964 | 4/1965 | Cottell et al. | 336/119 |
| 3,399,031 | 8/1968 | McCarthy | 423/305 |
| 3,945,618 | 3/1976 | Shoh | 366/118 |
| 4,016,436 | 4/1977 | Shoh | 310/8.2 |
| 4,252,844 | 2/1981 | Nesgood et al. | 427/213 |
| 4,268,641 | 5/1981 | Koenig et al. | 526/932 X |
| 4,278,692 | 7/1981 | Cassanelli et al. | 252/315.3 X |
| 4,584,124 | 4/1986 | Ong | 252/315.3 X |
| 4,674,286 | 6/1987 | Thatcher et al. | 60/740 |
| 4,675,194 | 6/1987 | Gaffney | 426/39 |
| 5,006,349 | 4/1991 | Dahlstrom et al. | 426/39 |
| 5,030,444 | 7/1991 | Hoyles et al. | 252/314 X |
| 5,296,166 | 3/1994 | Leong | 252/314 |
| 5,340,570 | 8/1994 | Wong et al. | 424/401 X |
| 5,466,570 | 11/1995 | Jagannathan et al. | 366/120 X |

FOREIGN PATENT DOCUMENTS

| | | |
|---|---|---|
| 0738509 | 10/1996 | European Pat. Off. . |

OTHER PUBLICATIONS

Dual Feed Sonolation, Sonic Corp, 1981, 4 pages.
Sonic Mixing Topics, Sonic Corp, Orifice Selection, 1980, 1 page.
Sonic Innovating Mixing Technology, Sonic Corp., 1994, 2 pages.
Ultrasonic Mixing, Sonic, 1981, 12 pages.
Typical Sonolator Applications, Sonic, 1975, 2 pages.
APV Homogenizers, Section 2, Bulletin N–1–100, APV Crepaco, Apr. 1989, 7 pages.

*Primary Examiner*—Richard D. Lovering
*Attorney, Agent, or Firm*—Martin B. Barancik

[57] ABSTRACT

A process for compatibly hydrating a fragmented solid which forms a gel with an aqueous composition, said process comprising:

a. generating a first aqueous composition and a second oily composition containing the said fragmented solid;

b. combining the first and second compositions in an at least the essential absence of air; and c. contacting the combined composition with a means for vibratorily mixing the combined composition, thereby causing the combined composition to be sufficiently mixed so as to hydrate the said fragmented solid to the extent that it is compatibilized into the composition and provides a stable gelled aqueous composition.

19 Claims, 2 Drawing Sheets

PROCESS FOR FORMING STABLE GELLED AQUEOUS COMPOSITION

BACKGROUND OF THE INVENTION

Adequate contacting of differing substances to bring about homogenous compositions has met with varying degrees of success throughout the ages. Various mixing devices have been developed including multibladed stirrers, baffled reactors combined with various stirring means, and the like. Compatible, stable dispersions and/or emulsions among liquid systems that are not soluble in each other at the specific concentrations have been formed by various means such as surfactant interaction, emulsifying aids, and the like, together with the appropriate mixing means.

Often the more difficult problem is forming a stable, compatible composition wherein one or more of the components remains in a heterogeneous phase, usually solid, with the bulk of the composition liquid. A further subcategory of these mixing problems is where one or more of the components of a liquid composition enters or is somewhere present in the process of preparing the final liquid composition in a heterogeneous phase, usually a solid. Unless such heterogeneous material is very readily soluble in the fluid medium, a compatible, stable, homogeneous final fluid composition is not readily obtained. This problem is particularly accentuated if the solid material changes physical characteristics when it is added to the fluid. For example, some fragmented materials such as powders, granules, crystals and the like tend to form agglomerates when first exposed to a fluid such as water. Illustrative examples of such materials include xanthan gum, acrylate polymers, acrylate acrylamide polymers, 2-hydroxy propyl ether guars, and carboxylic acid polymers. These agglomerates are difficult to break up through ordinary mixing means, are difficult to process and pass through standard chemical manufacturing equipment and may provide a final composition which is at least aesthetically displeasing, if not yet compatibilized. Still further, some of these solid materials also have a tendency to swell in size when exposed to the fluid, usually water. This makes the materials extremely difficult to handle in their highly concentrated, slurrified state prior to being combined with the main quantity of fluid composition. This seems to be particularly true for materials whose functions in the final composition is to supply a thickening effect. Such thickening effect is often achieved and/or accompanied by forming a gel. The gel seems to have a networked and/or cross linked structure which provides elasticity to the final composition as well as functioning as a thickener. Illustrative examples of such materials include xanthan gum, guar derived gums and 2-hydroxy propyl guar, acrylates, acrylate/acrylamide polymers and the like. Even in the final composition, the thickening agent may be non-evenly dispersed, insufficiently compatibilized and/or have a tendency to separate over time.

Such problems are even further exacerbated when the material also has a tendency to entrain air while in the swelling process. This additionally compounds the agglomeration issue, enhances the swelling, makes the actual processing and handling even more difficult, and finally, provides a final composition which appears to have voids, visual incompatibilities and differing levels of viscosity therein.

A new method has been discovered to wet fragmented solid materials, having one or more of these enumerated problems into a fluid, preferably aqueous composition, whereby the final composition is stable and compatible, has a continuous viscosity throughout and is visually pleasing. Additionally, the processing can be and is preferably continuous, runs in an essentially fluid manner and the processing equipment is readily maintained without plugging when not in use or during a recycle mode. The final composition which can be obtained is generally translucent and preferably transparent.

These goals are achieved by subjecting the fragmented solid and the aqueous stream to a means which vibrationally mixes the fragmented solid and aqueous stream to bring about efficient mixing in the essential or complete absence of air. The solid is thereby hydrated and successfully incorporated into the final composition.

SUMMARY OF THE INVENTION

In accordance with the invention there is a process for compatibly hydrating a fragmented solid which forms a gel with an aqueous composition, said process comprising a. generating a first aqueous composition and a second oily composition containing the said fragmented solid, b. combining the first and second compositions in an at least the essential absence of air, c. contacting the combined composition with a means for vibratorily mixing the combined composition, thereby causing the combined composition to be sufficiently mixed so as to hydrate the said fragmented solid to the extent that it is compatibilized into the composition and provides a stable gelled aqueous composition.

In further accordance with the invention, a process for systematically recycling various streams and/or shutting down the process allows the equipment to be immediately used without cleaning plugged fragmented solid from within the line.

DETAILED DESCRIPTION OF THE INVENTION

The fragmented solid processing is the key to the invention. These materials are, in general, difficulty hydratable. Examples of the fragmented solid which can be processed in accordance with the invention are various fragmented solid families such as, viscoelastic materials, suspending agents, and thickeners. Some specific materials can perform all these functions. Some such examples include the Carbomer® acrylate polymers available from Goodrich, guars, cellulosic ethers and the like. Particularly difficult to process are the gum-like materials, in particular, the xanthan gums. Generally manufactured in the powdered state, these materials are exemplary of all the previously mentioned difficulties in hydrating a fragmented solid. They tend to agglomerate when exposed to water. They swell in size substantially making it difficult to process. Finally, compounding the processing problem greatly, they entrain air into the swelled agglomerate. The entrainment of air generally increases as the concentration of xanthan gum used in the final composition increases. The remainder of this application in its detail will relate specifically to the xanthan gums but it should be noted that all the difficulty hydrated material, previously mentioned and particularly gum like materials, viscoelastic materials and/or thickeners are intended for coverage and well suited for successful implementation in the inventive process.

The devices which bring about the appropriate hydration of the difficulty hydratable fragmented solids are those means for bringing about extreme vibratory action on the aqueous composition bearing the fragmented solid. Several means are available for accomplishing this. The first is an in-line vibratory homogenizer which is compatible with continuous processing. This apparatus is an enclosed chamber having therein a knife edge, usually of a metallic nature. This knife edge is generally fixed at one end. The combined stream comprised of an aqueous stream and oily stream carrying the fragmented solid is brought into contact with the knife edge. Energy is transferred from the velocity of the stream to the knife edge causing it to vibrate in the ultrasonic spectrum. This vibrating knife edge provides extreme agitation and cavitation to the combined stream thereby bringing about a proper wetting of the fragmented solid and compatabilization with the combined stream. Due to the nature of the enclosed system, after air is pushed out of the system by the leading edge of the combined stream, there is essentially no air present in the system nor in the combined stream. The combined stream carrying the fragmented solid can be brought into contact at any point in the enclosed system prior to the contact of the combined stream with the knife edge and prior to the aperture which focuses the combined stream onto the knife edge. However, it is preferred to minimize the time the fragmented solid is in contact with the aqueous stream because of the previously mentioned difficulties. Therefore, it is preferred to combine the aqueous stream and the oily stream immediately prior to contact with the knife edge or entering an aperture prior to the knife edge.

After compatibilization and hydration of the fragmented solid, the remainder of the aqueous soluble material, such as surfactants, can be added.

The knife edge is vibratorily moved by any energy providing source. However, it is preferably vibrated by the stream contacting the surface of the blade inside the chamber. Since the streams are under pressure to bring about movement, this energy is transferred to the knife edge which causes it to vibrate in the ultrasonic frequency range, thus creating a cavitation effect at the knife edge. Although we do not wish to be bound by any theory, it is believed that it is within this cavitation field that the high energy mixing effect takes place.

This is an example of a means for vibratorily mixing in an enclosed, continuous process.

A further example of utilization of a vibrating means can occur in a batch process which is open to the atmosphere wherein an electromechanical vibratory generator is used to hydrate and compatibilize the fragmented solid into an aqueous system. An aqueous composition is prepared in an open reactor with water soluble components therein. An oily composition containing the fragmented solid is fed into the aqueous composition in a manner which brings about as little introduction of air into the aqueous composition as possible. Generally, the oily stream is in relatively small quantities so as to bring about a minimum of air introduction. Concomitantly, with the introduction of the second stream, an electromechanical, vibratory generator already present or is inserted into the combined composition and allowed to vibrate at a frequency which hydrates the fragmented solid and compatibilizes the composition.

Other means which brings about the appropriate vibratory frequency to hydrate and compatibilize can be employed. The preferred means is the in line knife edge in a chamber. This apparatus is marketed by Sonic Corporation of Stratford, Conn. as the "Sonolator". The aqueous composition can be combined with the "oily" stream carrying the fragmented solid immediately before an aperture which leads to the sonication chamber. Inside the mixing (sonication) chamber, the kinetic energy of the high velocity liquid stream is converted into high intensity mixing energy by utilizing a physical phenomenon known as "jet-edge tone". The jet of process liquid under pressure is forced through an elliptical aperture at a high velocity (generally 300 fps (feet per second) or more) and is directed at the edge of a blade-like obstacle in its path. Between the aperture and blade-like obstacle, the jet of liquid sheds vortices perpendicular to the original flow vector. The shedding pattern is stable, and alternates such that a steady oscillation in the ultrasonic range of about 20,000 to about 100,000 Hertz or more, occurs within the liquid. The stresses set up within the fluid by ultrasonic oscillations can and preferably do cause the fluid to cavitate in the ultrasonic frequency range. It is the high level of cavitation combined with the shear and turbulence within the mixing chamber which shatters the product particles and emulsifies liquids, when necessary.

In order to maintain the proper frequency of oscillation of the knife edge, the stream should be moving through the line under an appropriate pressure. This pressure is at least partially dependent upon the viscosity of the composition, flow rates and aperture area. However, in general, a pressure of at least about 300 psig, preferably at least about 350 psig is employed. The maximum pressure is determined by the nature of the equipment, processing and safety factors. The frequency of oscillation for the knife edge is also at least partially dependent upon the viscosity of the composition, flow rates and aperture area. Generally, at least about 20,000 Hertz, preferably at least about 30,000 Hertz can bring about appropriate hydration and compatibilizing. The uppermost oscillatory frequency generally about 100,000 Hertz is at least partially determined by viscosity, flow rate and aperture area.

The nature of the aqueous stream is that it should have an appropriate quantity of the water soluble materials which could create issues if added later in the processing streams. Additionally, materials which could magnify the hydration and/or compatilization issues of the fragmented solid should be omitted or present in small quantities. The aqueous composition may also comprise at this time various quantities of water soluble materials present in the final composition such as chelating agents, preservatives, colors, ultraviolet stabilizers, pH adjusters, and the like which might be difficult to add later in the process, particularly because of the quantity of the material involved.

The fragmented solid is dispersed in a separate oily stream prior to bringing the oily composition and aqueous composition into contact. By "oily" is meant a composition which is essentially non-soluble in water or the quantity of water into which it will be contacted. In the context of a watery composition as previously described, such "oily" compositions can have components such as free fatty acids, fragrances, organic emulsifiers, organic preservatives, oils in general, petrolatums, antibacterial agents such as Triclosan and trichlorocarbanilide, and the like, as well as the fragmented solid. Although generally not necessary, it is sometimes preferred to add a small amount of surfactant, usually common to the final composition and preferably anionic to make the fragmented solid more readily processable and fluidized for processing through the equipment.

After passing through the mixing chamber, the compatibilized mixture continues through the processing line and the remainder of the active components added. For example, the remainder of the aqueous solution materials can be added in additional streams while maintaining the mixing through the use of static mixers so that the composition remains compatibilized. Various other materials particular to the final composition can be added at various points including immediately before entering a holding vessel prior to filling the final container.

In general, after the vibratory mixing means, the bulk, if not all of the surfactants, are added to the combined stream. The surfactants which can be added include the following: Soap, a long chain alkyl or alkenyl, branched or normal carboxylic acid salt such as sodium, potassium, ammonium or substituted ammonium salt, can be present in the composition. Exemplary of long chain alkyl or alkenyl are from about 8 to about 22 carbon atoms in length, specifically about 10 to about 20 carbon atoms in length, more specifically alkyl and most specifically normal, or normal with little branching. Small quantities of olefinic bond(s) may be present in the predominantly alkyl sections, particularly if the source of the "alkyl" group is obtained from a natural product such as tallow, coconut oil and the like.

Other surfactants can be present in the composition as well. Examples of such surfactants are the anionic, amphoteric, nonionic and cationic surfactants. Examples of anionic surfactants include but are not limited to alkyl sulfates, anionic acyl sarcosinates, methyl acyl taurates, N-acyl glutamates, acyl isethionates, alkyl sulfosuccinates, alkyl phosphate esters, ethoxylated alkyl phosphate esters, trideceth sulfates, protein condensates, mixtures of ethoxylated alkyl sulfates and the like.

Alkyl chains for these surfactants are $C_8$–$C_{22}$, preferably $C_{10}$–$C_{18}$, more preferably $C_{12}$–$C_{14}$.

Anionic nonsoap surfactants can be exemplified by the alkali metal salts of organic sulfate having in their molecular structure an alkyl radical containing from about 8 to about 22 carbon atoms and a sulfonic acid or sulfuric acid ester radical (included in the term alkyl is the alkyl portion of higher acyl radicals). Preferred are the sodium, ammonium, potassium or triethanolamine alkyl sulfates, especially those obtained by sulfating the higher alcohols ($C_8$–$C_{18}$ carbon atoms), sodium coconut oil fatty acid monoglyceride sulfates and sulfonates; sodium or potassium salts of sulfuric acid esters of the reaction product of 1 mole of a higher fatty alcohol e.g., tallow or coconut oil alcohols) and 1 to 12 moles of ethylene oxide; sodium or potassium salts of alkyl phenol ethylene oxide ether sulfate with 1 to 10 units of ethylene oxide per molecule and in which the alkyl radicals contain from 8 to 12 carbon atoms, sodium alkyl glyceryl ether sulfonates; the reaction product of fatty acids having from 10 to 22 carbon atoms esterified with isethionic acid and neutralized with sodium hydroxide; water soluble salts of condensation products of fatty acids with sarcosine; and others known in the art.

Zwitterionic surfactants can be exemplified by those which can be broadly described as derivatives of aliphatic quaternary ammonium, phosphonium, and sulfonium compounds, in which the aliphatic radicals can be straight chain or branched and wherein one of the aliphatic substituents contains from about 8 to 18 carbon atoms and one contains an anionic water-solubilizing group, e.g., carboxy, sulfonate, sulfate, phosphate, or phosphonate. A general formula for these compounds is:

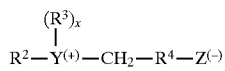

wherein $R^2$ contains an alkyl, alkenyl, or hydroxy alkyl radical of from about 8 to 18 carbon atoms, from 0 to about 10 ethylene oxide moieties and from 0 to I glyceryl moiety; Y is selected from the group consisting of nitrogen, phosphorus, and sulfur atoms; $R^3$ is an alkyl or monohydroxyalkyl group containing 1 to about 3 carbon atoms; X is I when Y is a sulfur atom and 2 when Y is a nitrogen or phosphorus atom, $R^4$ is an alkylene or hydroxyalkylene of from 0 to about 4 carbon atoms and Z is a radical selected from the group consisting of carboxylate, sulfonate, sulfate, phosphonate, and phosphate groups.

Examples include: 4-[N,N-di(2-hydroxyethyl)-N-octadecylammonio]-butane-1-carboxylate; 5-[S-3-hydroxypropyl-S-hexadecylsulfonio] -3 hydroxypentane-1-sulfate; 3-[P,P-P-diethyl-P 3,6,9 trioxatetradecyl-phosphonio]-2-hydroxypropane-1-phosphate; 3[N,N-dipropyl-N-3 dodecoxy-2-hydroxypropylammonio]-propane-1-phosphonate; 3(N,N-di-methyl-N-hexadecylammonio) propane-1-sulfonate; 3-(N,N-dimethyl-N-hexadecylammonio)-2-hydroxypropane-1-sulfonate; 4-(N,N-di(2-hydroxyethyl)-N-(2 hydroxydodecyl) ammonio]-butane-1-carboxylate; 3-[S-ethyl-S-(3-dodecoxy-2-hydroxypropyl) sulfonio]-propane-1-phosphate; 3-(P,P-dimethyl-P-dodecylphosphonio)-propane-1-phosphonate; and 5-[N,N-di(3-hydroxypropyl)-N-hexadecylammonio]-2-hydroxy-pentane-1-sulfate.

Examples of amphoteric surfactants which can be used in the compositions of the present invention are those which can be broadly described as derivatives of aliphatic secondary and tertiary amines in which the aliphatic radical can be straight chain or branched and wherein one of the aliphatic substituents contains from about 8 to about 18 carbon atoms and one contains an anionic water solubilizing group, e.g., carboxy, sulfonate, sulfate, phosphate, or phosphonate. Examples of compounds falling within this definition are sodium 3-dodecylaminopropionate, sodium 3-dodecylaminopropane sulfonate, N-alkyltaurines, such as the one prepared by reacting dodecylamine with sodium isethionate according to the teaching of U.S. Pat. No. 2,658,072, N-higher alkyl aspartic acids, such as those produced according to the teaching of U.S. Pat. No. 2,438, 091, and the products sold under the trade name "Miranol" and described in U.S. Pat. No. 2,528,378. Other amphoterics such as betaines are also useful in the present composition.

Examples of betaines useful herein include the high alkyl betaines such as coco dimethyl carboxymethyl betaine, 1 auryl dimethyl carboxy-methyl betaine, lauryl dimethyl alpha-carboxyethyl betaine, cetyl dimethyl carboxymethyl betaine, lauryl bis-(2-hydroxyethyl)carboxy methyl betaine, stearyl bis-(2-hydroxypropyl) carboxymethyl betaine, oleyl dimethyl gamma-carboxypropyl betaine, lauryl bis-(2-hydro-xypropyl) alpha-carboxyethyl betaine, etc. The sulfobetaines may be represented by coco dimethyl sulfopropyl betaine, stearyl dimethyl sulfopropyl betaine, amido betaines, amidosulfobetaines, and the like.

Many cationic surfactants are known to the art. By way of example, the following may be mentioned:
  stearyldimenthylbenzyl ammonium chloride;
  dodecyltrimethylammonium chloride;
  nonylbenzylethyldimethyl ammonium nitrate;
  tetradecylpyridinium bromide;
  laurylpyridinium chloride;
  cetylpyridinium chloride
  laurylpyridinium chloride;
  laurylisoquinolium bromide;
  ditallow(Hydrogenated)dimethyl ammonium chloride;
  dilauryldimethyl ammonium chloride; and
  stearalkonium chloride.

Additional cationic surfactants are disclosed in U.S. Pat. No. 4,303,543 see column 4, lines 58 and column 5, lines 1–42, incorporated herein by references. Also see CTFA Cosmetic Ingredient Dictionary, 4th Edition 1991, pages 509–514 for various long chain alkyl cationic surfactants; incorporated herein by references.

Nonionic surfactants can be broadly defined as compounds produced by the condensation of alkylene oxide groups (hydrophlic in nature) with an organic hydrophobic compound, which may be aliphatic or alkyl aromatic in nature. Examples of preferred classes of nonionic surfactants are:

1. The polyethylene oxide condensates of alkyl phenols, e.g., the condensation products of alkyl phenols having an alkyl group containing from about 6 to 12 carbon atoms in either a straight chain or branched chain configuration, with ethylene oxide, the said ethylene oxide being present in amounts equal to 10 to 60 moles of ethylene oxide per mole of alkyl phenol. The alkyl substituent in such compounds may be derived from polymerized propylene, diisobutylene, octane, or nonane, for example.

2. Those derived from the condensation of ethylene oxide with the product resulting from the reaction of propylene oxide and ethylene diamine products which may be varied in composition depending upon the balance between the hydrophobic and hydrophilic elements which is desired. For example, compounds containing from about 40% to about 80% polyoxyethylene by weight and having a molecular weight of from about 5,000 to about 11,000 resulting from the reaction of ethylene oxide groups with a hydrophobic base constituted of the reaction product of ethylene diamine and excess propylene oxide, said base having a molecular weight of the order of 2,500 to 3,000, are satisfactory.

3. The condensation product of aliphatic alcohols having from 8 to 18 carbon atoms, in either straight chain or branched chain configuration with ethylene oxide, e.g., a coconut alcohol ethylene oxide condensate having from 10 to 30 moles of ethylene oxide per mole of coconut alcohol, the coconut alcohol fraction having from 10 to 14 carbon atoms. Other ethylene oxide condensation products are ethoxylated fatty acid esters of polyhydric alcohols (e.g., Tween 20-polyoxyethylene (20) sorbitan monolaurate).

4. Long chain tertiary amine oxides corresponding to the following general formula:

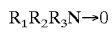

$$R_1R_2R_3N \rightarrow 0$$

wherein $R_1$ contains an alkyl, alkenyl or monohydroxy alkyl radical of from about 8 to about 18 carbon atoms, from 0 to about 10 ethylene oxide moieties, and from 0 to 1 glyceryl moiety, and, $R_2$ and $R_3$ contain from 1 to about 3 carbon atoms and from 0 to about 1 hydroxy group, e.g., methyl, ethyl, propyl, hydroxy ethyl, or hydroxy propyl radicals. The arrow in the formula is a conventional representation of a semipolar bond. Examples of amine oxides suitable for use in this invention include dimethyldodecylamine oxide, oleyl-di(2-hydroxyethyl) amine oxide, dimethyloctylamine oxide, dimethyldecylamine oxide, dimethyltetradecylamine oxide, 3,6,9 trioxaheptadecyldiethylamine oxide, di(2-hydroxyethyl)-tetradecylamine oxide, 2-dodecoxyethyldimethylamine oxide, 3-dodecoxy-2-hydroxypropyldi(3-hydroxypropyl)amine oxide, dimethylhexadecylamine oxide.

5. Long chain tertiary phosphine oxides corresponding to the following general formula:

$$RR'R''P \rightarrow 0$$

wherein R contains an alkyl, alkenyl or monohydroxyalkyl radical ranging from 8 to 20 carbon atoms in chain length, from 0 to about 10 ethylene oxide moieties and from 0 to 1 glyceryl moiety and R' and R'' are each alkyl or monohydroxyalkyl groups containing from 1 to 3 carbon atoms. The arrow in the formula is a conventional representation of a semipolar bond. Examples of suitable phosphine oxides are: dodecyldimethylphosphine oxide, tetradecylmethylethylphosphine oxide, 3,6,9-trioxaoctadecyldimethylphosphine oxide, cetyldimethylphosphine oxide, 3-dodecoxy-2-hydroxypropyldi(2-hydroxyethyl) phosphine oxide stearyldimethylphosphine oxide, cetylethyl propylphosphine oxide, oleyldiethylphosphine oxide, dodecyldiethylphosphine oxide, tetradecyldiethylphosphine oxide, dodecyldipropylphosphine oxide, dodecyldi(hydroxymethyl) phosphine oxide, dodecyldi(2-hydroxyethyl)phosphine oxide, tetradecylmethyl-2-hydroxypropylphosphine oxide, oleyldimethylphosphine oxide, 2-hydroxydodecyldimethylphosphine oxide.

6. Long chain dialkyl sulfoxides containing one short chain alkyl or hydroxy alkyl radical of 1 to about 3 carbon atoms (usually methyl) and one long hydrophobic chain which contain alkyl, alkenyl, hydroxy alkyl, or keto alkyl radicals containing from about 8 to about 20 carbon atoms, from 0 to about 10 ethylene oxide moieties and from 0 to 1 glyceryl moiety. Examples include: octadecyl methyl sulfoxide, 2-ketotridecyl methyl sulfoxide, 3,6,9-trioxaoctadecyl 2-hydroxyethyl sulfoxide, dodecyl methyl sulfoxide, oleyl 3-hydroxypropyl sulfoxide, tetradecyl methyl sulfoxide, 3 methoxytridecylmethyl sulfoxide, 3-hydroxytridecyl methyl sulfoxide, 3-hydroxy-4-dodecoxybutyl methyl sulfoxide.

When using a continuous process, the equipment eventually must be shut down or at least put into a recycle mode "holding pattern" for short periods of time. For most processes, this does not pose a major problem since the pumps can merely be shut down and the lines optionally opened and drained. However, with the tendency of the fragmented solid to agglomerate, swell, and potentially entrain any air that is present, such activity(s) can bring about plugged lines, wasted compositional material, and lengthy line cleaning procedures. Recycle modes are of significance when a pump might break down or a holding vessel reaches its capacity and the like.

Various compositions can be prepared in this way including personal care compositions, shampoos, fabric cleansers, hard surface cleansers, lotions, creams, and the like. The process is particularly useful where the final composition is desirable to have a final viscosity brought about by the addition of a thickening, viscosity effecting agent which initially is present in the process as a fragmentized solid such as a xanthan gum.

BRIEF DESCRIPTION OF DRAWINGS

The following FIGURES are present to help further explain the process.

FIG. 1 shows a cutaway view of the Sonolator vibratory homogenizer. The aqueous stream enters the mixing chamber, 3, prior to the aperture, 2, under pressure through pipe 4. Generally this stream contains various water soluble materials other than the major surfactants utilized in a cleansing solution. Examples of such materials include chelating agents such as coloring agents, ultraviolet inhibiting agents, acidity adjusting agents and the like. The "oily" stream containing, for example, the organic fragrance, emulsifier (if desirable), antibacterial agent such as Triclosan or trichlorocarbanilide and the like as well as the fragmented solid(s), in particular, a xanthan gum, enters the mixing chamber prior to the aperture through pipe 5. The aperture 2 is generally at about 0.020 inches square or larger. The maximum size of the aperture is dependent upon the flow rate employed. A higher aperture area generally needs a higher flow rate to maintain pressure. Generally for the systems being processed, it is usually not necessary to exceed an aperture area of about 0.026 inches square. Within a short distance of the aperture is the knife edge, 1. The kinetic energy of the combined stream of the aqueous and oily materials is transferred to the knife edge, 1, which oscillates in a frequency of at least about 20,000, Hertz, preferably at least about 30,000 Hertz. The maximum frequency of oscillation is at least partially dependent upon viscosity, the design of the homogenizer and the safety margins desired. Generally, the frequency of oscillation need not go beyond about 60,000 Hertz. The hydrated, fragmented powder is now compatibilized into the stream exiting 6 and carried and under pressure to other points along pipe, 23. See FIG. 2 where various other composition components can be added, particularly surfactants, and particle beads carrying emollients.

FIG. 2 shows the process including the "Sonolator", homogenizer, described in detail in FIG. 1. FIG. 2 is described with respect to certain compositions. However, any surfactant bearing final composition with an initial introduction of a fragmented solid is contemplated for processing in this manner.

Figure 1:
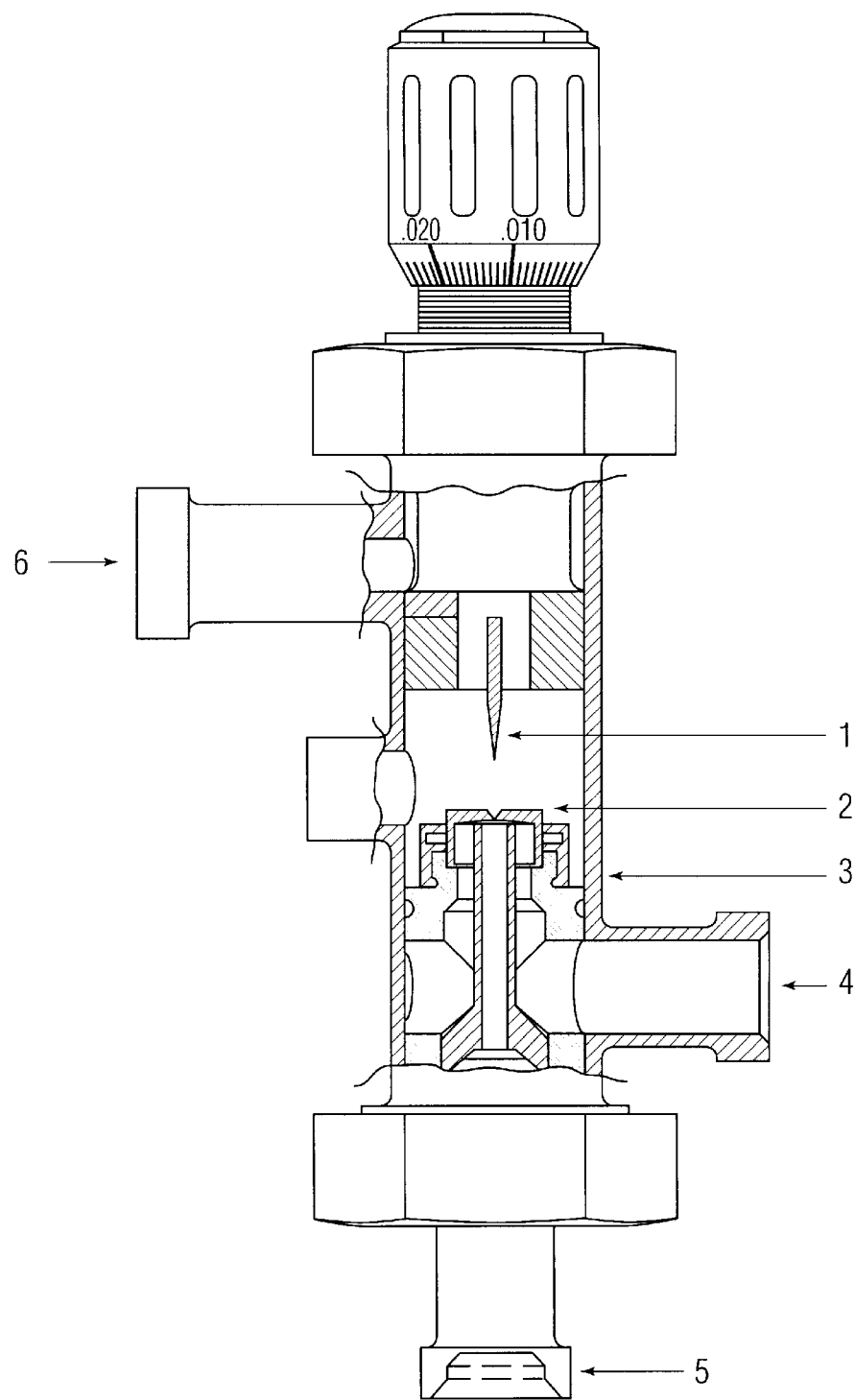
FIG. 1 shows the in line mixing chamber known as a "Sonolator".

A container, 20 holds the water phase which is comprised of water, chelating agent, color(s), ultraviolet stabilizer such as benzophenone, pH adjustment agents such as citric acid, sodium hydroxide and the like to bring about a desired pH. A second container, 26, holds the oily phase which is comprised of an organic fragrance, an emulsifier for the final composition where it is appropriate to use one, preservatives, an antibacterial agent such as Triclosan, trichlorocarbanilide, ortho chloro xylene and the like where an antibacterial effect is desired, an emollient such as a free fatty acid having from about 10 to about 20 carbon atoms, a fatty acid ester, a silicone such as dimethicone and the like. The fragmented solid is also present and is fluidized by the oily composition so that it is pumpable to the "Sonolator"0 homogenizer, 24. In order to increase fluidization of the oily phase, a small quantity of a surfactant may also be present in the oily stream. Examples of the fragmented solid include xanthan gum, 2 hydroxy propyl guar, and acrylate containing polymers. Of particular interest are the xanthan gums, particularly because of their previously noted issues when in contact with water. Of the xanthan gums, one of the most difficult ones to solubilize is known as Keltrol-T, available from Kelco Labs. The water phase passes through line 56 to the homogenizer, 24 prior to the aperture, under a pressure of from about 325 to about 375 psig, preferably about 350 psig. The oil phase is fed through line 28 to the homogenizer, 24 under a pressure of from about 350 to about 400 psig, preferably about 375 psig, where the two streams are combined prior to the aperture and subject to the oscillatory vibratory mixing from the knife edge and the other effects, previously noted within the homogenizer. The stream containing the hydrated, compatibilized fragmented solid, now in at least a highly dispersed solubilized form, is moved under pressure through line 23 to a point wherein a water solution of a water soluble surfactant, particularly an anionic surfactant, stored in vessel 31 is fed under relatively low pressure about 125 to about 175 psig, preferably about 150 psig into line 33 and passed into line 23 wherein it is mixed with the main combined stream by a static mixer, 35. The combined stream carrying the surfactant and the highly hydrated, well-dispersed and solubilized fragmented solid is carried further through pipe 23 wherein a second soluble surfactant, preferably an amphoteric surfactant such as a betaine or a nonionic surfactant such as an alkylated polyglycoside or even a further anionic or cationic surfactant or a mixture of any or all of these is in a holding tank, 38, and added to line 41 at a low pressure of about 125 to about 175 psig, preferably about 150 psig into line 23 and thereafter passing through a static mixer, 43 to achieve appropriate mixing. It should be noted that the system, particularly pipe 23, is enclosed, therefore, no excess air is added to the composition. When the system starts up fresh, all or essentially all the air is pushed out of the system by the moving liquid front. At this point, any further materials can be added, particularly solid materials which are to remain as solids thereby forming a heterogeneous system with the fluid, liquid composition. For example, beads carrying emollients can be added to the composition at this time from storage vessel 45, via a screw feeder through pipe 46 gently entering a vessel 47 wherein there is a mixer bringing about integration of the beads from vessel 45 but without instilling any significant quantities of air into the fluid liquid composition. From vessel 47 the contents are transported to a finish, holding tank 52 wherein the contents are fed into a final fill line, 54.

It should be noted that each of the vessels 20, 26, 31 and 38 are equipped respectively with a recycle line 22, 59, 62 and 65, and a valve which can open said recycle line 67, 69, 71 and 73 respectively, when it is necessary to recycle the materials rather than moving them into pipe 23.

In starting up the process, all the aqueous systems are fed into pipe 23 followed by the "oily" phase of vessel 26. This minimizes the exposure of the fragmented solid to the aqueous system and flushes out the air in the pipes prior to contact with the fragmented solid. The recycle mode is used at start up to flush these lines as well. The recycle is also used when there is a problem during processing with the flow rates or the pressure above certain ranges or the finishing, holding tank is full. It is preferred when entering the recycle mode to initially recycle the surfactant holding vessels, that is, those vessels after the "Sonolator" homogenizer, followed by the oil phase and lastly, the water phase. This routine minimizes any agglomeration or swelling. When the process requires shutting down, the first portion stopped is the oil phase followed by the various aqueous streams. The goal is to maintain the pipes free of agglomerated solid which would require lengthy cleaning and deplugging efforts.

Figure 2:
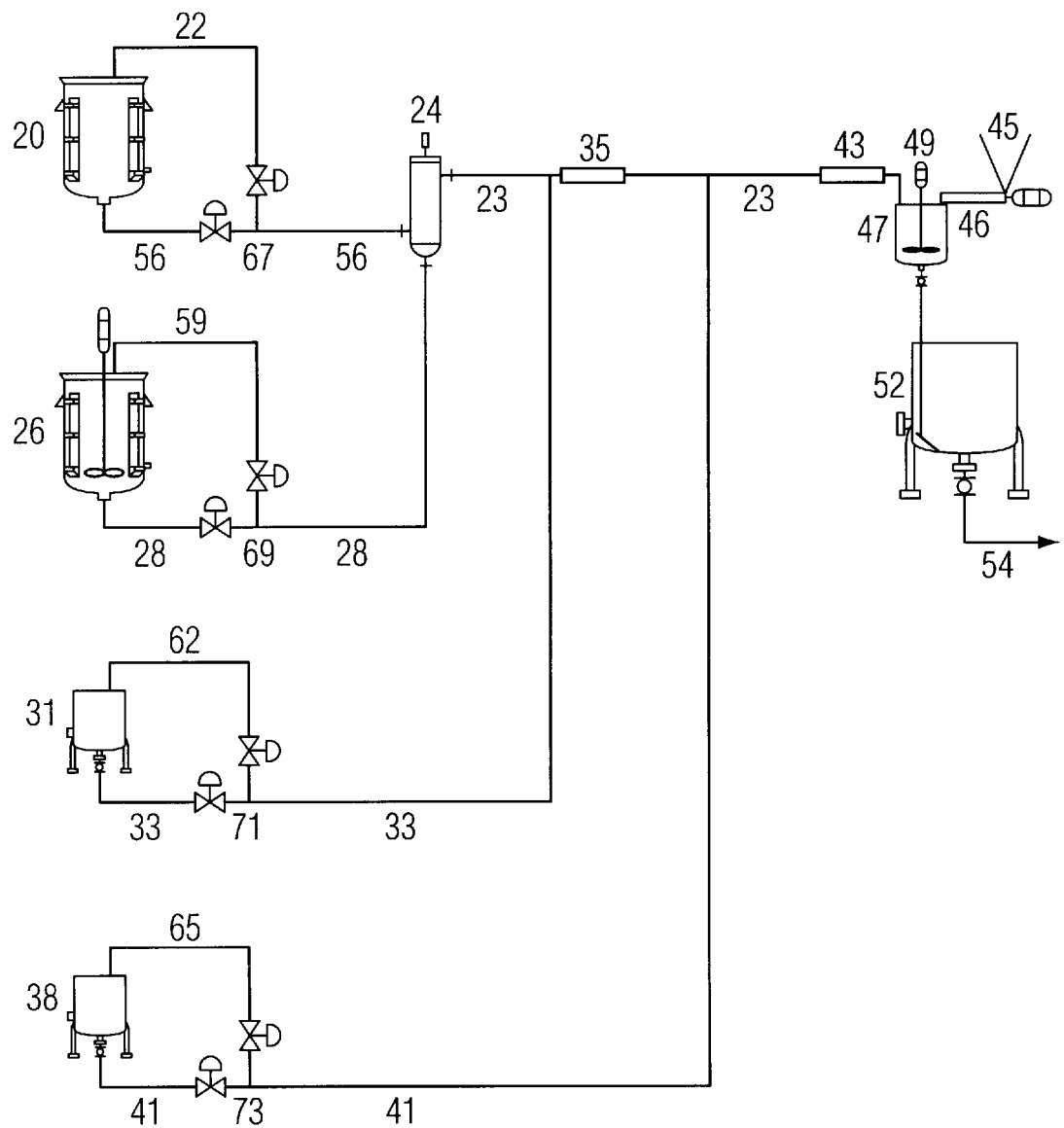
FIG. 2 shows a particular process for the preparation of a composition utilizing a fragmented solid. This process is intended to be illustrative of the numerous processes which can be successfully implemented by the process of this invention and not be unduly restrictive thereof.

The process is now illustrated by a specific working example whereby a specific composition is prepared utilizing the process of the invention. This example is intended to merely exemplify and not narrow the broad concept of the invention. Numbers in the example refer to the same numbered portions in FIG. 2.

EXAMPLE 1

After a proper start up procedure as outlined above, an aqueous composition containing water soluble chelator, colors, preservatives, ultraviolet inhibitor and pH adjusting agent to bring about a pH of about 5.0 in 20 is fed through line 56 to line 23 at a pressure of 350 psig and a flow rate of 54 pounds/minute. This quantity is approximately 54 wt. % of the final composition. From vessel 26 the "oily" phase containing the organic fragrance, the emulsifier, Triclosan and xanthan gum, available as Keltrol T from Keltrol Labs is fed through line 28 at a rate of 4.6 pounds/minute and a pressure of about 375 psig. In order to provide assurity of nonagglomeration and minimization of other problems, approximately 1.85% of the anionic surfactant sodium laureth sulfate (30 wt. % active, 70 wt. % water) is also present in the oily phase. The total oily phase as measured by weight percent of the final composition is about 4.6 wt. %. The oily phase and aqueous phase are combined in the homogenizer prior to an elliptical aperture of 0.020 inches square under a pressure of about 350 psig. The knife edge is vibrating at a frequency of about 20,000 to about 100,000 Hertz. After a residence time in the homogenizer Model No. BT-DF, the hydrated, dispersed compatibilized aqueous composition is passed through line 23 to the point where an aqueous solution of sodium laureth sulfate in vessel 31 is fed into line 23 at a rate of about 35 pounds/minute and a pressure of about 150 psig and mixed with the previous aqueous streams at static mixer 35. The quantity of sodium laureth sulfate and water fed into line 23 is approximately 35 wt. % of the final composition. As the composition passes down line 23, the contents of vessel 38 is brought into line 23 by line 41 at a flow rate of about 6 pounds/minute and a pressure of about 150 psig. This vessel holds the remainder of the surfactants, such as betaine, preferably cocoamidopropylbetaine, and a cationic polymer such as polyquaterum 6 as well as the remainder of any water soluble materials. These contents of vessel 38 are approximately 6% of the final composition. The contents of vessel 38 are mixed in line 23 with static mixer 43 and enter bead premix vessel 47 having mixer 49 therein. To vessel 47 are added particles at 0.5 pounds/minute, atmospheric pressure carrying emollients for the system which are slowly mixed with the final aqueous composition. These particles are about 0.5 wt. % of the final composition. The composition then flows into finishing holding vessel 52 where it then enters the fill line, 54. In the final composition the particles are maintained in place over an extended period of time by the viscoelastic behavior of the xanthan gum containing composition.

The contents of the final composition are the following approximately:

| Component | wt. % |
|---|---|
| Sodium Laureth sulfate (2EO) | 10.4 |
| Cocoamidopropyl betaine | 1.7 |
| Xanthan gum | 1.1 |
| Fragrance | 0.7 |
| PEG-40 Hydrogenated Castor Oil Trideceth-9 | 0.07 |
| Encapsulated emollient particles | 0.3 |
| Preservatives | 0.25 |
| Dipropylene glycol | 0.27 |
| Triclosan | 0.15 |
| Citric acid anhydrous | 0.1 |
| UV protectant | 0.05 |
| Colors | Trace |
| Water | Balance |

It should be understood that other surfactant systems, and fragmented solids can be used in place of the specific ones enumerated in this example as noted throughout the specification. Different compositions based on varying wt. % in the final composition can also be readily prepared by the process of this invention.

The process of the invention is particularly useful for preparing compositions having relatively large quantities of water, generally over about 50 wt. %, preferably over about 60, 70 and even 80 wt. % water. These compositions are particularly useful in the personal care area and preferably have surfactant(s) and mixture of surfactants therein. Uses of such compositions include skin cleansing, hair cleansing and the like. It is preferred to have a translucent final composition as measured by a turbidimeter, preferably before any solid material such as the aforementioned particle carrying emollients is added. It is more preferred to have transparent final composition as measured by turbidimeter. In general the usage of a 2100P Turbidimeter by Hach, Loveland, Colo. can separate a translucent from transparent composition. Although subject to some interpretation as to precisely what is transparent as opposed to translucent, the crossover between transparent and translucent occurs in the about 20–25 NTU range of the turbidimeter.

A viscosity of the final composition can vary from about 2,000 to about 12,000 centipoise and can be measured on a Brookfield RVT using a spindle 4 at 10 rpm at room temperature. A more preferred viscosity is from about 2,500 to about 11,000 centipoise.

Generally very small quantities of fragmented solid present problems if not properly compatilized. Quantities as small as about 0.2 wt. %, preferably above about 0.4 wt. % can be present. Xanthan gums appear to provide the most difficult issues.

What is claimed is:

1. A process for compatibly hydrating a fragmented solid which forms a gel with an aqueous composition, said process comprising:
   a. generating a first aqueous composition and a second oily composition containing the said fragmented solid;
   b. combining the first and second compositions in at least the essential absence of air; and
   c. contacting the combined composition with a means for vibratorily mixing the combined composition, thereby causing the combined composition to be sufficiently mixed so as to hydrate the said fragmented solid to the extent that it is compatibilized into the composition and provides a stable gelled aqueous composition.

2. The process in accordance with claim 1 wherein the means is an electromechanical oscillator and the process is a batch process.

3. The process in accordance with claim 2 wherein the fragmented solid is selected from the group consisting of xanthan gum, 2 hydroxy propyl ether guar and acrylate containing polymers.

4. The process in accordance with claim 3 wherein the fragmented solid is a gummy material.

5. The process in accordance with claim 4 wherein the fragmented solid is a xanthan gum.

6. The process in accordance with claim 5 wherein the composition is at least about 70 wt. % water.

7. The process in accordance with claim 6 wherein a surfactant or mixture of surfactants are added to the combined composition after vibratorily mixing.

8. The process in accordance with claim 7 wherein the surfactant or mixture of surfactants is at least about 5 wt. % of the composition.

9. The process in accordance with claim 6 wherein the xanthan gum is present in quantities which will agglomerate and swell when in the presence of moisture.

10. The process in accordance with claim 9 wherein the said gelled aqueous composition is used in the personal care area.

11. The process in accordance with claim 1 wherein the process is continuous and the means is an in line oscillating knife edge.

12. The process in accordance with claim 11 wherein the fragmented solid is selected from the group consisting of xanthan gum, 2 hydroxy propyl ether guar and acrylate containing polymers.

13. The process in accordance with claim 12 wherein the fragmented solid is a gummy material.

14. The process in accordance with claim 13 wherein the gummy material is a xanthan gum.

15. The process in accordance with claim 14 wherein the composition is at least about 70 wt. % water.

16. The process in accordance with claim 15 wherein a surfactant or mixture of surfactants are added to the combined composition after vibratorily mixing.

17. The process in accordance with claim 16 wherein the surfactant or mixture of surfactants is at least about 5 wt. % of the composition.

18. The process in accordance with claim 16 wherein the xanthan gum is present in quantities which will agglomerate and swell when in the presence of moisture.

19. The process in accordance with claim 18 wherein the said gelled aqueous composition is used in the personal care area.

* * * * *